(12) United States Patent
Albus et al.

(10) Patent No.: US 8,161,679 B2
(45) Date of Patent: Apr. 24, 2012

(54) OPEN OCEAN FLOATING ALGAE FARM

(76) Inventors: James Sacra Albus, Kensington, MD (US); Alverto Daniel Lacaze, Germantown, MD (US); Karl Nicholas Murphy, Rockville, MD (US)

( * ) Notice: Subject to any disclaimer, the term of this patent is extended or adjusted under 35 U.S.C. 154(b) by 127 days.

(21) Appl. No.: 12/643,170

(22) Filed: Dec. 21, 2009

(65) Prior Publication Data
US 2010/0154298 A1    Jun. 24, 2010

Related U.S. Application Data

(63) Continuation of application No. 12/341,990, filed on Dec. 22, 2008.

(51) Int. Cl.
*A01H 13/00* (2006.01)
(52) U.S. Cl. .......................................................... 47/1.4
(58) Field of Classification Search ................ 47/1.4, 47/59 R, 62 E, 62 R; 56/8; 119/223, 200, 119/201; 114/256, 244
See application file for complete search history.

(56) References Cited

U.S. PATENT DOCUMENTS 6,328,165 B1 * 12/2001 Baker et al. .................... 209/235
2007/0209278 A1 *  9/2007 Becker .......................... 47/59 R

* cited by examiner

*Primary Examiner* — Kristen C Hayes
(74) *Attorney, Agent, or Firm* — White-Welker & Welker, LLC; Matthew T. Welker, Esq.

(57) ABSTRACT

An open ocean floating algae farm built around a ship. The ship provides propulsion power for navigation, storage capacity for materials and algae products, machinery for harvesting and processing the algae, housing for crew, and facilities for maintenance of the floating farm. The invention is also comprised of transparent tubes that circulate a broth of seawater saturated with $CO_2$, nutrients, and algae. The circulation path flows from the ship through the tubes and back to the ship where the algae is filtered out to be processed. The fields of transparent tubes circulating the algae broth are supported by a square matrix of pressurized tubes filled with seawater. This matrix is neutrally buoyant and submerged just below the ocean surface. The internal pressure in the tubes causes the matrix to be stiff in the horizontal plane, but flexible in the vertical dimension so as to conform to long ocean waves.

12 Claims, 9 Drawing Sheets

OPEN OCEAN FLOATING ALGAE FARM

CROSS REFERENCE TO RELATED APPLICATIONS

This application claims priority from and is a continuation of U.S. patent application Ser. No. 12/341,990, entitled "Method and system for robotic algae harvest", filed on 22 Dec. 2008. The benefit under 35 USC §119(e) of the United States provisional application is hereby claimed, and the aforementioned application is hereby incorporated herein by reference.

FEDERALLY SPONSORED RESEARCH

Not Applicable

SEQUENCE LISTING OR PROGRAM

Not Applicable

TECHNICAL FIELD OF THE INVENTION

The present invention relates generally to a method and system for growing and harvesting algae for use in bio-fuels. More specifically, the present invention relates to a method and system for robotic algae harvest for use in bio-fuels and other applications.

BACKGROUND OF THE INVENTION

More than enough clean energy to supply all of humanity's needs falls on the Earth every day in the form of sunlight. The problem is how to capture this energy. Much of the solar energy is translated into evaporation of seawater to produce clouds, rain, and wind. Some of this can be captured by hydroelectric dams and windmills. Some is captured by plants through photosynthesis. Most is simply reflected back into space.

One problem with solar energy is that it is spread thinly over the surface of the earth. The energy density of sunlight is about Capturing a lot of energy requires a large area. Thus, solar cells are an expensive because it takes so many of them. Solar cells cost about $1000 per square meter. Solar power generators using mirrors are complex and require a large field of reflectors. Perhaps the most practical way to capture solar energy is through photosynthesis.

Photosynthesis is a process by which carbon atoms are absorbed from $CO_2$ molecules in the atmosphere, and oxygen molecules are released. When plants (or their fossilized byproducts such as oil or gas) are burned, oxygen molecules are absorbed and $CO_2$ molecules are released back into the atmosphere. Burning also releases the energy that was stored in the plant by photosynthesis. Burning fossil fuel releases $CO_2$ that was absorbed millions of years ago, and produces a net increase in atmospheric $CO_2$. However, burning recently grown biomass releases recently absorbed $CO_2$. This is a carbon neutral cycle. There is no net increase in greenhouse gases. Thus, fuel from biomass is a carbon neutral energy source.

Biofuels are safe to store, easy to transport, and clean to burn. Bidies nearly as energy dense as gasoline, and much less toxic when spilled. And there are no toxic materials or heavy metals involved such as are present in the batteries used in hybrid and electric vehicles. Estimates are that conversion of cellulose to biofuels will become commercially viable within two to five years. It could become carbon neutral within a decade or two.

In the long term however, biomass production cannot be a long-term replacement for oil, coal, and natural gas until several more fundamental problems are solved.

The biggest problem lies in the vast amount of biomass required and the limited amount of unused real estate that is appropriate for biomass production. Most of the world's best farmland is already under cultivation for food crops, and using the Earth's remaining forests and wetlands for biomass production is not an environmentally sound solution. Although the amount of land under cultivation can be increased, and increases in agricultural production can be expected from genetic engineering and improved fertilizers, increased acreage will grow ever more costly as population growth transforms farmland into cities and suburbs. Doubling the amount of land under cultivation is probably not possible.

A second and related problem is that demand for fuel will drive up the price of food in the marketplace so long as food and fuel compete for the same cropland. Ethanol production from corn has already had a significant impact on price of corn and products made from corn. The effect of rising prices is spilling over into other cereal crops such as wheat, soybeans, and even sorghum.

A third problem is that there is a limited supply of water in most regions of the world not already under cultivation. Major irrigation projects are enormously expensive, and often are destructive to the environment. Water for irrigation is subject to seasonal variations and drought. Water is already a limiting resource in many parts of the world.

In the near term, current methods of farming for biomass require fossil fuel for plowing, planting, and harvesting. Until the fuel for biomass production is derived from the biomass produced, this process is not carbon neutral.

Finally, there is a limited growing season in regions more than 50 degrees from the equator.

Until these problems are overcome, fuel from biomass cannot become a long-term alternative to fossil fuel.

SUMMARY OF THE INVENTION

The present invention teaches a novel open ocean floating algae farm for the production of bio-fuels from algae that overcomes the shortcomings of prior art solutions.

The major hurdles with microalgae harvesting include: Algae varieties rich in oils do not survive well in open ponds because the have a hard time competing with naturally occurring algae; Optimal algae grows is dependent on the temperature of the water; Algae cultures require large amounts of water; and Dissolving sufficient amounts of $CO_2$ from the air require large air-water surfaces.

The present invention teaches a sustainable process for growing algae for the production of biofuels. The recent interest in the use of agriculture products as replacements for petrochemical products (biodegradable plastics, ethanol for transportation, etc) has had unintended consequences (rise in food prices) and unseen environmental impact (carbon emissions). The proposed project may enable a bio-fuel that does not impact critical food prices while having a more environmentally friendly carbon implant. In fact, this project is expected to make use of sequestered carbon in the growth of the algae.

World demand for biofuels will expand at a nearly 20 percent annual pace to 92 million metric tons in 2011, despite recent concerns about the impact of biofuels on the environment and food supplies. Market expansion will come from a more than doubling of the world market for bioethanol, and even faster increases in global biodiesel demand. Despite the growing size of the world's largest producers, the proliferation of new companies and rapid expansion of the biofuel industry overall combined to limit the top nine producers to just a 30 percent share of the market in 2006. This lack of dominant companies will enable Robotic research to compete in this rabidly growing market.

The proposed system referred to herein as the open ocean floating algae farm (also referred to as "OOFAF"). A biological leaf built around the hull of an oil tanker ship. The ship provides propulsion power for navigation, storage capacity for materials and algae products, machinery for harvesting and processing the algae, housing for crew, and facilities for maintenance of the floating farm. The leaf is comprised of transparent tubes that circulate a broth of seawater saturated with $CO_2$, nutrients, and algae. The circulation path flows from the ship through the tubes and back to the ship where the algae is filtered out to be processed, and nutrients and $CO_2$ are added to the water. The circulation is driven by wave energy captured from the ocean. The fields of transparent tubes circulating the algae broth would be supported by a square matrix of pressurized tubes filled with seawater.

This matrix would be neutrally buoyant and would be submerged just below the ocean surface. The internal pressure in the tubes would cause the matrix to be stiff in the horizontal plane, but flexible in the vertical dimension so as to conform to long ocean waves. This would prevent the transparent tubes from folding or bunching up from the forces of waves, wind, and differential currents. The ship would have normal propulsion capabilities to allow the algae farm to navigate out of shipping lanes and away from hurricanes. The pressurized support matrix would be attached to the sides and rear of the ship, and towing forces would be distributed throughout the matrix by a series of steel cables.

The system and method taught by the present invention produces multiple products and generates multiple sources of income from: biodiesel; ethanol; carbon credits; tax subsidies; and dry algae briquettes. The present invention does not require significant changes to the current infrastructure, does not require large landmasses, and each individual technology is currently available.

It is therefore an objective of the present invention to teach an economically and environmentally sustainable system and method for the production of algae for bio-fuel use. The present invention is responsive to the USDA's call for economically and environmentally sustainable production of biomass material to be used as fuel, including but not limited to, ethanol.

It is also therefore an objective of the present invention to teach the use of algae that will not have adverse effects on food prices, nor result in a 'bio-fuel carbon debt' unlike bio-fuels products based on food products.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION OF THE INVENTION

Figure 1:
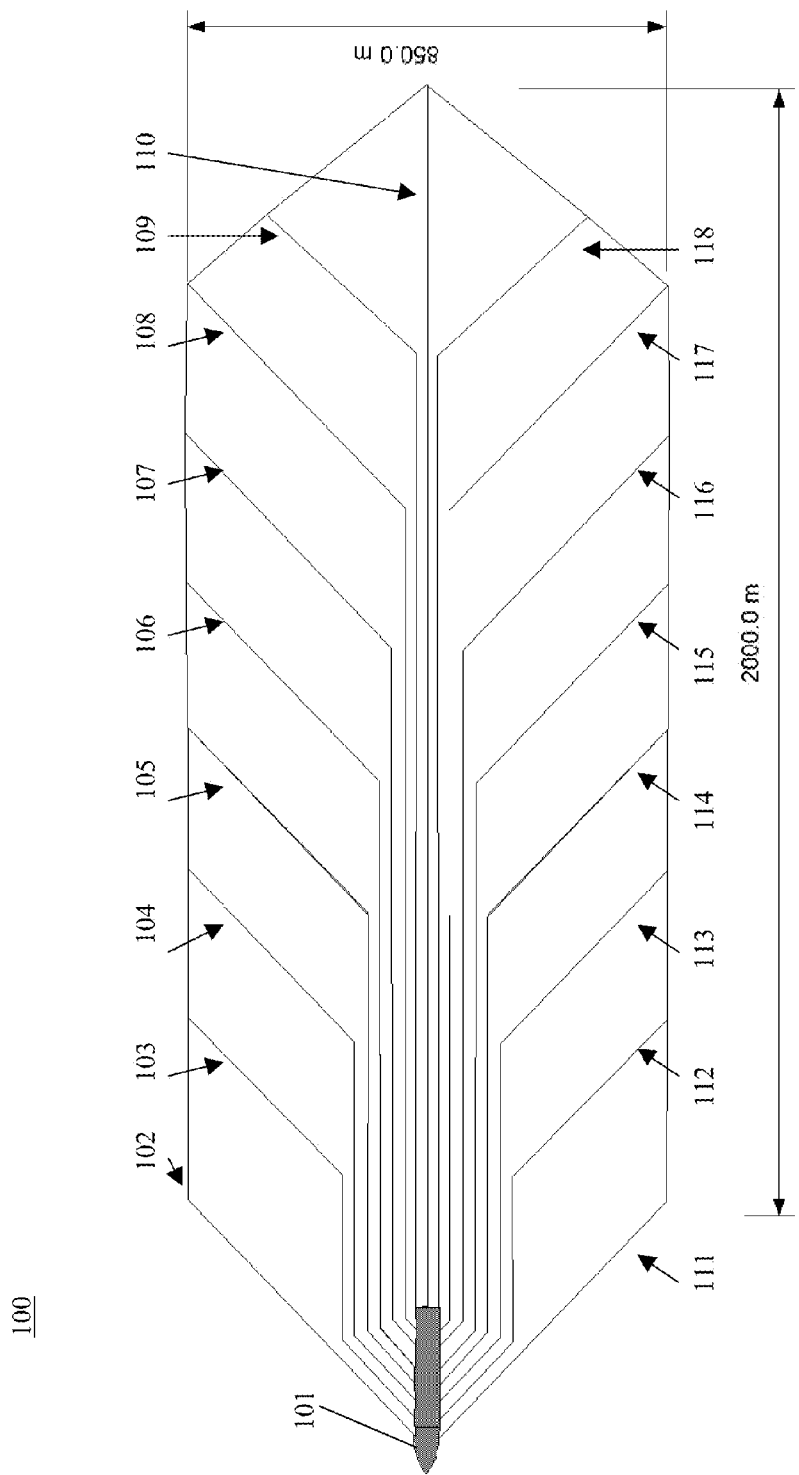
FIG. 1 illustrates one possible design of the present invention.

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention.

Referring to the Figures, it is possible to see the various major elements constituting the apparatus of the present invention. The present invention is a method and system for an open ocean floating algae farm.

One way that biomass production could be expanded dramatically would be to farm the equatorial oceans. Fifty percent of the surface of the globe lies within 30 degrees of the equator and 70% of this region is water. The equatorial oceans contain about 178 million $km^2$ of virtually empty space—an area almost twice that of the entire United States (including Alaska.) The equatorial oceans are warm and days are nearly 12 hours long 365 days per year. Within 30 degrees of the equator, the average solar power at the surface of the earth (averaged over 24 hours) is about 400 watts/$m^2$. Thus, the amount of solar energy falling on the equatorial oceans is equivalent to about $7 \times 10^{16}$ watts, or 70 billion megawatts. If only one tenth of one percent of this energy could be captured, it would produce the equivalent of 70 million megawatts, or roughly 20 times the average total world energy consumption for all forms of energy, including oil, natural gas, coal, nuclear, and hydroelectric.

There are many varieties of seaweed that cover a spectrum from single cell algae to giant kelp plants. In between these extremes are many varieties of multi-cell algae. Some of these aggregate into floating mats. Other species such as kelp anchor themselves to rocks in shallow water. Many varieties of seaweed grow aggressively under the right environmental conditions consisting of nutrient rich water and sunlight. Seaweed has long been harvested for food, fertilizer, cosmetics, medicines, and biotechnology in many places around the world. The Department of Energy's National Renewable Energy Laboratory (NREL) in Golden Colo. has identified over 300 species of algae as possible sources of biofuel. In waters as far apart as China and Ireland, coastal waters are often covered by thick floating mats of multi-cell algae. Many forms of algae have the capacity to cover vast regions of ocean with a layer of green.

Algae is currently under active consideration by researchers, entrepreneurs, and venture capitalists as a source of biofuel. Algae stores energy in the form of lipids that can be easily converted into oil for biodiesel or ethanol fuel. Growing algae has potential for oil production both because of its fast growth rate and the high oil content of some varieties. Some species of algae are so rich in oil that it accounts for over 50% of their dry mass.

Venture capitalists firms are estimating that commercial scale algae farms and conversion plants could produce between 2,000 and 20,000 gallons of biodiesel per acre per year. One company claims they can produce up to 180,000 gallons of biodiesel per year per acre at a cost of 59 cents per gallon or $25 per barrel. For comparison, biodiesel produced from soybeans produces only 50 gals/acre/yr. Biodiesel from palm oil yields 600 gals/acre/yr.

The problem with farming the oceans for energy production is that there is limited coastal real estate that is suitable for farming. Natural algae and kelp beds grow in coastal shallows where nutrients from silt on the bottom are constantly agitated by wave action. The deep oceans are devoid of nutrients necessary to grow biomass.

Many types of seaweed such as kelp must be attached to underwater structures such as rocks on the bottom. This further limits the available acreage. Artificial kelp mooring systems have been developed, but these are vulnerable to storm damage in the open ocean.

One solution to these problems is to build large floating algae farms consisting of transparent mats filled with nutrient rich water that would be capable of surviving the environment of the open oceans. These would be equipped with propulsion units that would enable them to navigate clear of shipping lanes and avoid heavy weather. They would convert wave energy into pumping action to circulate growing algae suspended in water through filtration stations and processing plants that would collect the algae and convert it into a precursor to biofuel. These farms would be visited periodically by tanker ships that would up-load the biofuel precursor products, and off-load equipment and supplies, including liquid fertilizer and solid or liquid $CO_2$. The fertilizer and $CO_2$ would be dissolved in the water to promote rapid growth of the algae.

The design for a floating biofuel farm must enable it to maintain its structural integrity on the open ocean environment. It must be rigid in the horizontal plane but flexible in the vertical so as to ride smoothly over the top of the waves without folding or kinking. It must be capable of navigating out of shipping lanes and away from approaching storms. It must be capable of sinking below the surface in heavy weather and rising back to the surface when the storms have passed.

One possible design would be to mimic the structure of a biological leaf built around the hull of an oil tanker ship. There are many tanker ships in the current inventory that could be converted at a minimal cost or a ship could be specifically designed for the purpose.

The ship would provide propulsion power for navigation, storage capacity for materials and algae products, machinery for harvesting and processing the algae, housing for crew, and facilities for maintenance of the floating farm.

The first embodiment of the present invention is an algae farm attached to the tanker ship with the algae broth circulating in transparent tubes.

Now referring to FIG. 1, the top view of a leaf shaped algae farm 100 structured around a converted Panamax oil tanker ship 101 is shown. The ship 101 is shown at the left. The outlines show the fields of transparent tubes 102-118 that circulate a broth of seawater saturated with $CO_2$, nutrients, and algae. The circulation path flows from the ship 101 through the tubes 102-118 and back to the ship 101 where the algae is filtered out to be processed, and nutrients and $CO_2$ are added to the water. The circulation is driven by wave energy captured from the ocean.

Figure 2:
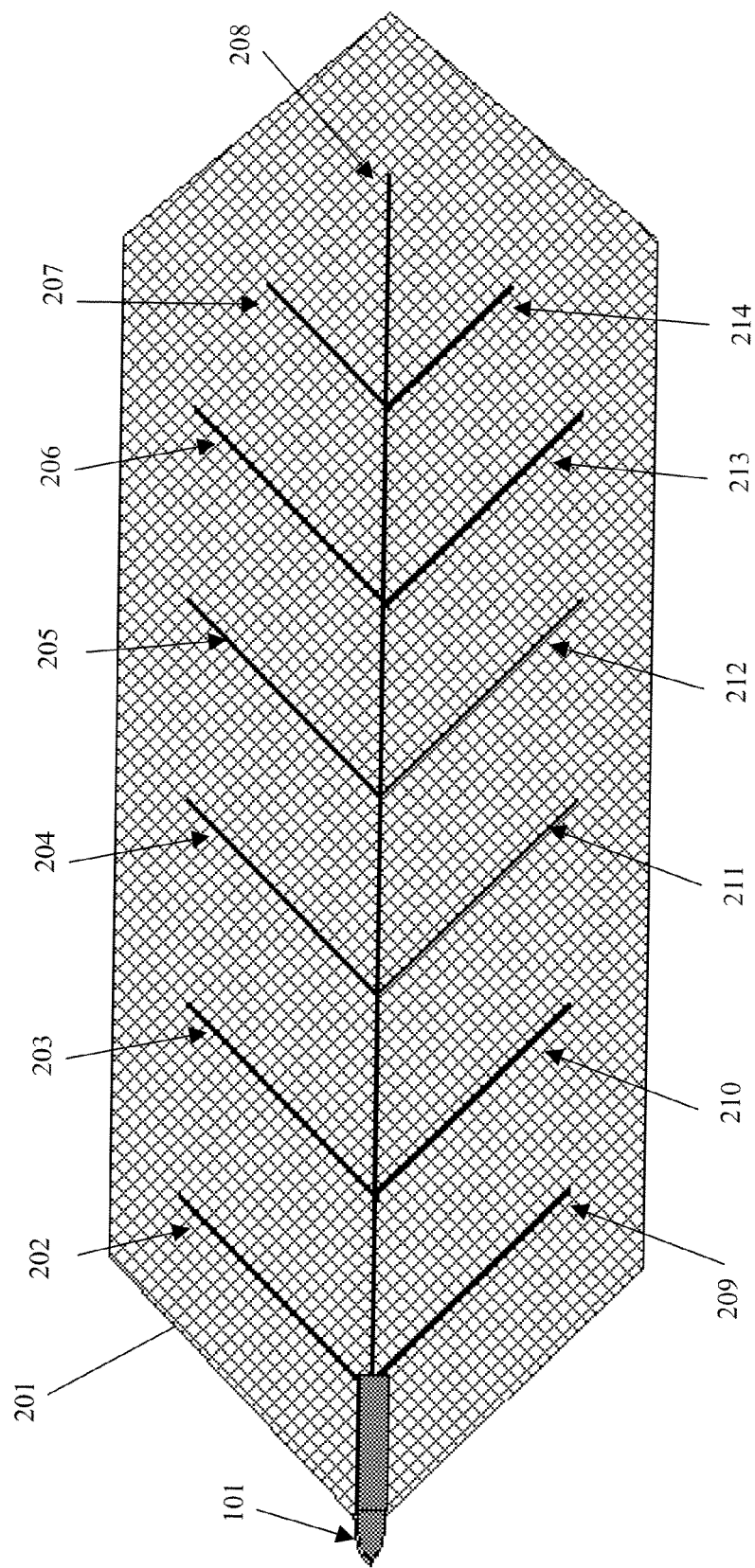
FIG. 2 illustrates a neutrally buoyant truss structure consisting of fabric tubes inflated with seawater attached to the ship with steel or Kevlar cables.

The fields of transparent tubes 102-118 circulating the algae broth would be supported by a square matrix of pressurized tubes 201 filled with seawater as shown in FIG. 2. This matrix 201 would be neutrally buoyant and would be submerged just below the ocean surface. The internal pressure in the tubes would cause the matrix 201 to be stiff in the horizontal plane, but flexible in the vertical dimension so as to conform to long ocean waves. This would prevent the transparent tubes 102-118 from folding or bunching up from the forces of waves, wind, and differential currents.

The ship 101 would have normal propulsion capabilities to allow the algae farm to navigate out of shipping lanes and away from hurricanes. The pressurized support matrix 201 would be attached to the sides and rear of the ship 101, and towing forces would be distributed throughout the matrix 201 by a series of steel cables 202-214 as shown in FIG. 2.

Figure 3A:
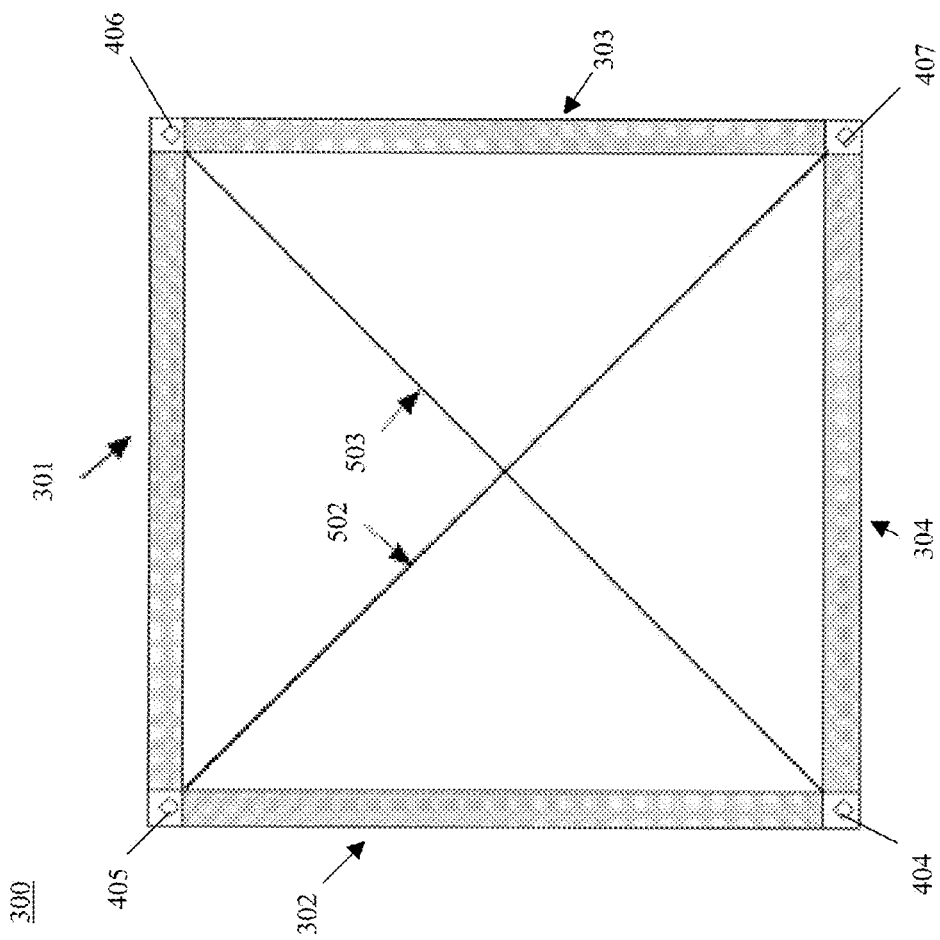
FIG. 3a illustrates a top view of 20 m element of the square structural truss that provides horizontal stiffness and supports the transparent tubes filled with algae broth showing the pressurized tubes, corner connectors, and crossed steel or Kevlar cables that provide diagonal structural stiffness.
Figure 3B:
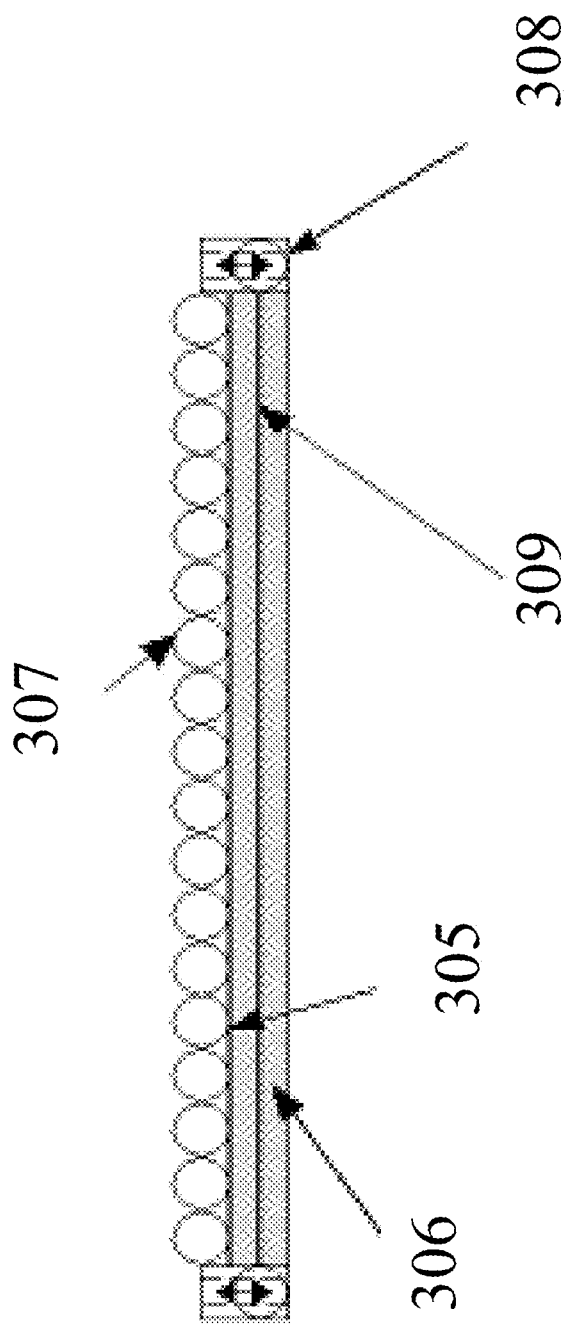
FIG. 3b is an end view of 20 m element of the square structural truss showing a ribbon of 18 transparent tubes supported by a fabric base that circulate the algae filled water.

A single 20 m×20 m element 300 of the support matrix 201 is shown in FIGS. 3a and 3b. The pressurized fabric tubes 301-304 are one meter in diameter and filled with seawater pressurized to about 3 psi. A pressurized fabric tube of this design will withstand a compressive force of more than 1200 pounds before crushing. The length to diameter ratio of 20:1 enables the pressurized fabric tubes to resist Euler buckling. Higher internal pressure could be used to increase the tubes' resistance to compressive force. However, higher pressure also increases the hoop stress in the walls of the tubes, and hence increases the required strength of the fabric. 3 psi seems a reasonable engineering compromise. Empirical testing can verify this design choice.

As shown in the side view of FIG. 3(b), there is a waterproof fabric base 305 stretched over the top of the pressurized tubes 306. This supports the transparent tubes 307 that circulate the algae broth, and also serves as a barrier to the vertical flow of seawater. Switchable flow check valves 308 located in the corner connectors of the 20 m×20 m elements 300 can be electronically switched open or closed to cause wave energy to pump water upward for submerging, or downward for surfacing. If seawater is pumped down, the structure will rise to the surface. If seawater is pumped up, the structure will submerge. To submerge completely the transparent tubes 307 must also be purged of any gas ($CO_2$ or $O_2$) that may have accumulated inside.

Figure 4:
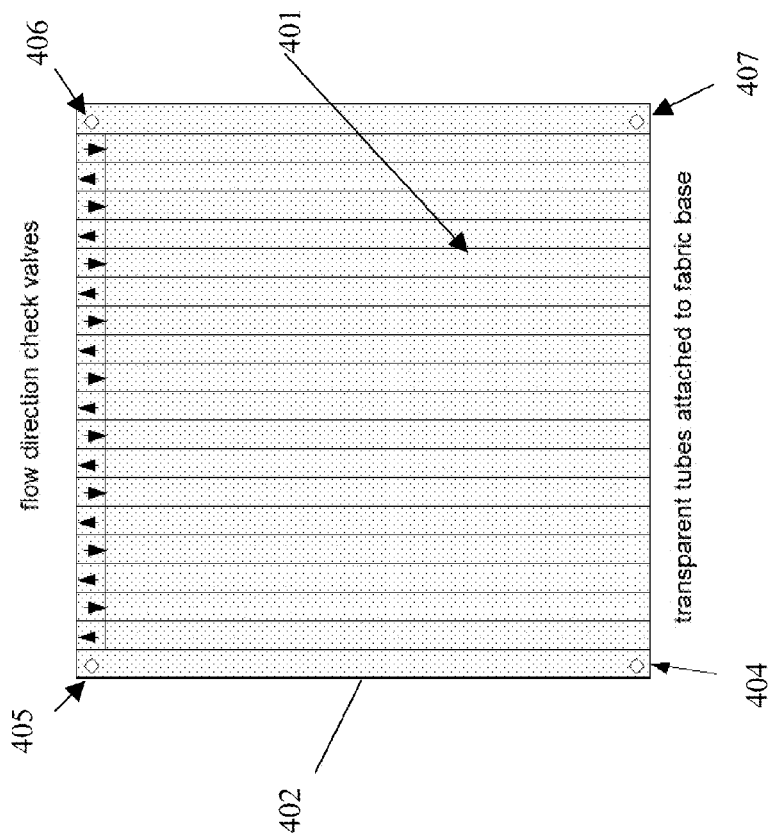
FIG. 4 illustrates a top view of a 20 m square cell with transparent tubes and directional valves that use wave energy to pump water and algae through the transparent tubes.

FIG. 4 shows a top view of a 20 m square cell 400 with transparent tubes 401 and directional valves 402 that use wave energy to pump water and algae through the transparent tubes 401. This top view of the structure also shows the transparent tubes 401 attached to the fabric base 403 that is penetrated in the corners by the switchable check valves 404, 405, 406, and 407.

It may be necessary from time to time to clean the transparent tubes, as algae may become attached to the inside of the tubes. For this task, a robot can be designed to move through the insides of the tubes and scrub them using energy provided by wave action to power itself.

Figure 5:
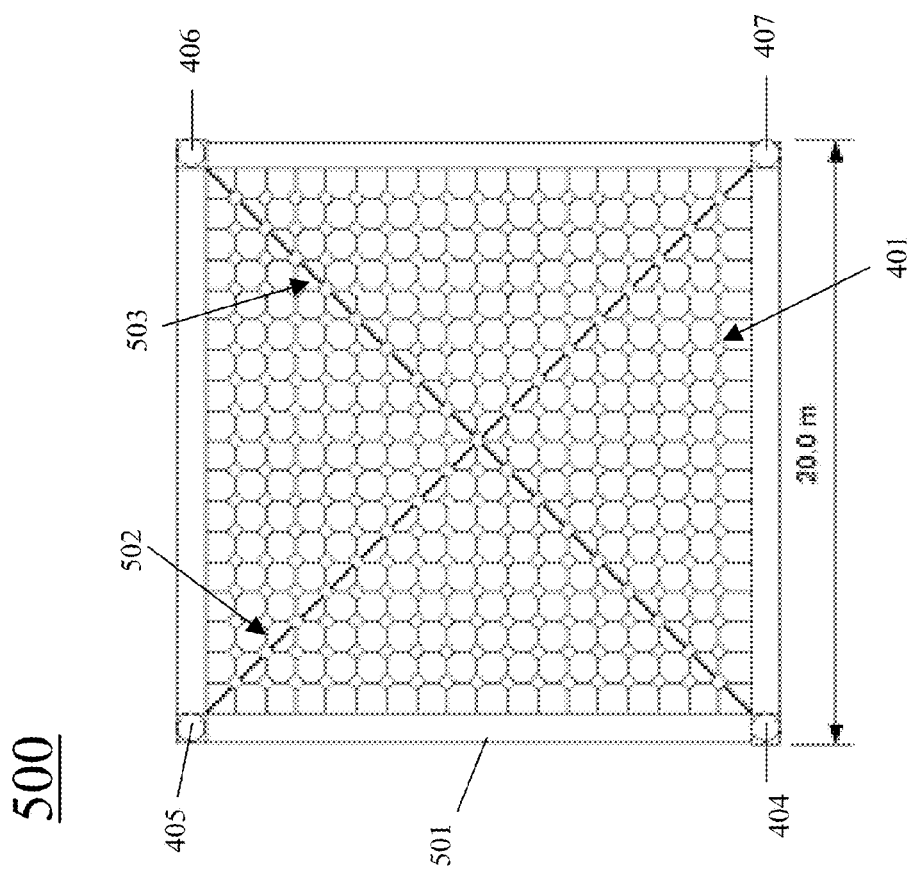
FIG. 5 illustrates around the periphery of the pressurized matrix is a 20 m barrier with a floatation collar to prevent breaking waves from pounding the transparent tubes.

Now referring to FIG. 5, around the periphery of the pressurized matrix 500 is a 20 m barrier with a floatation collar 501 to prevent breaking waves from pounding the transparent tubes 401. A design for this floatation collar is shown in FIG. 5.

Figure 6:
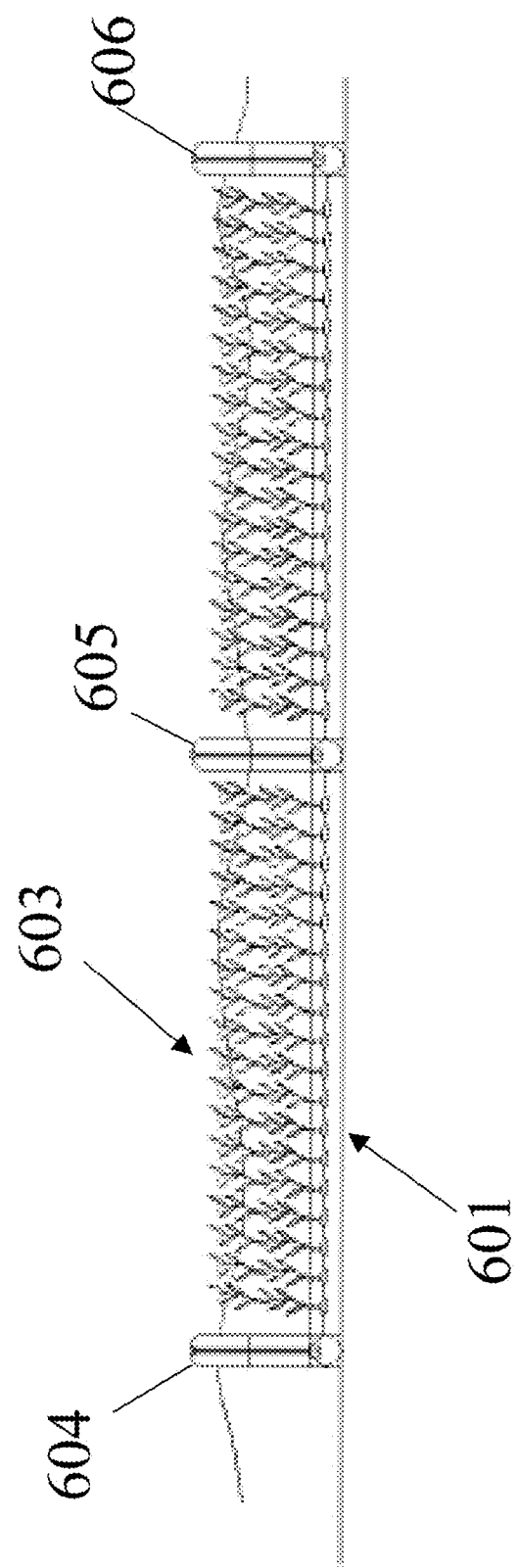
FIG. 6 illustrates this matrix of squares that have a fabric bottom to separate the fertilized water in the lagoon above from the ocean water below.

The second embodiment of the present invention is a kelp lagoon with an open top and a closed bottom with kelp attached to hold fasts. The alternate embodiment of the 20 m×20 m matrix element for an open ocean kelp farm is shown in FIGS. 6-8. In this case, the matrix element has a waterproof fabric 601 stretched over the bottom. The pressurized matrix is made slightly negatively buoyant, and is supported at a desired depth of about 3 m by a matrix of floatation buoys. When surrounded by a floatation collar, this provides a lagoon of nutrient rich seawater.

FIGS. 6-8 show a biomass farm designed for kelp. This structure is a square matrix 2 km on a side, surrounded by a floatation collar 602. A waterproof fabric bottom 601 on this structure confines the nutrient rich water in the lagoon 603. The square shape of the lagoon 603 is maintained by a square matrix of 20×20 m square truss elements 501 consisting of 1 m diameter compression tubes made from dycron or nylon fabric. These fabric tubes would fill with seawater and pressurized to a modest pressure of about 3 psi. The 20×20 m linear truss elements 501 would be maintained square by cables 502 and 503 between diagonal corners. This structure would be neutrally buoyant. It would be constrained to hover at a desired depth by a series of floatation buoys 604, 605, and 606 that are suspended above each vertex. Ballast provided by valves and winches in each vertex enables the matrix to maintain a controlled depth. This can be adjusted by changing the length of steel cables 309 between the floatation buoys 604, 605, and 606 and the vertices. If necessary, the entire structure can be made negatively buoyant so as to sink beneath the surface to avoid storms.

The square matrix of the farm would be maintained parallel to the ocean surface at a depth of about 3 m by an array of flotation buoys 604, 605, and 606. It would be maintained rigid in the horizontal plane by a square grid of 20 m×20 m tubular frames 500 of the design shown in FIG. 5.

Now referring to FIG. 6, a 20 m×20 m frame formed of 1 m diameter tubes filled with water and pressurized to 3 psi is illustrated. At this pressure, these tubes are able to resist compressive force of about 3770 lb. The frames are cross-braced by cables 502 and 503 and supported by floatation buoys at the four corners at a depth that is optimal depth for growing kelp (about 3 m.)

These frames would be constructed from 1 m diameter Dacron or Kevlar fabric tubes filled with water pressurized to about 3 psi. At this pressure, each tube would be able to withstand a compressive force of about 3000 lb. and would have a sufficient diameter-to-length ratio to prevent buckling. These tubes would provide adequate compressional forces to maintain the overall shape in the horizontal plane.

This matrix of squares would have a fabric bottom 601 to separate the fertilized water in the lagoon above from the ocean water below. This however means that the entire structure provide minimum impedance to the currents induced by the wave action. The horizontal impedance is minimal since the bottom is horizontal. However, the vertical impedance will depend on the flexibility of the matrix in the vertical direction. Therefore the stiffness of the fabric used for the pressurized tubes must be optimized to permit flexing but not buckling.

However, for the structure to conform to the vertical wave motion the stiffness of the fabric chosen should be such that bending forces induced by wave action are easily absorbed without buckling. Otherwise the corners must provide compliance in the connections (e.g., with a bellows) to prevent transferal of bending forces through the joints.

The corners of the 20 m×20 m frames would be cubical or spherical in shape, with compliance in the connections to prevent transferal of bending forces through the joints. Opposite corners of the frame would be connected by tensioned cables 502 and 503 so as to maintain squareness in the horizontal plane while allowing flexibility in the vertical direction to accommodate wave motion. A 2 km square algae or kelp farm would contain about 10,000 20×20 m square frames.

A square grid has several advantages. One is that it results in long straight rows of constant width that are ideal for harvesting vehicles. Another is that a square grid is easy to manufacture and maintain. All the tubes and vertices are identical in size and shape, so that most of the components can be mass-produced.

A waterproof fabric bottom 601 is stretched from the processing plants to the floatation collar beneath the grid of 20×20 m frames. This bottom maintains fertilized water around the algae. It also protects the algae from species of fish that graze on it, and enables the farm to raise fish that are compatible with the algae. Whether or not the bottom is bonded to the underside of the square truss structure is to be determined.

Figure 7A:
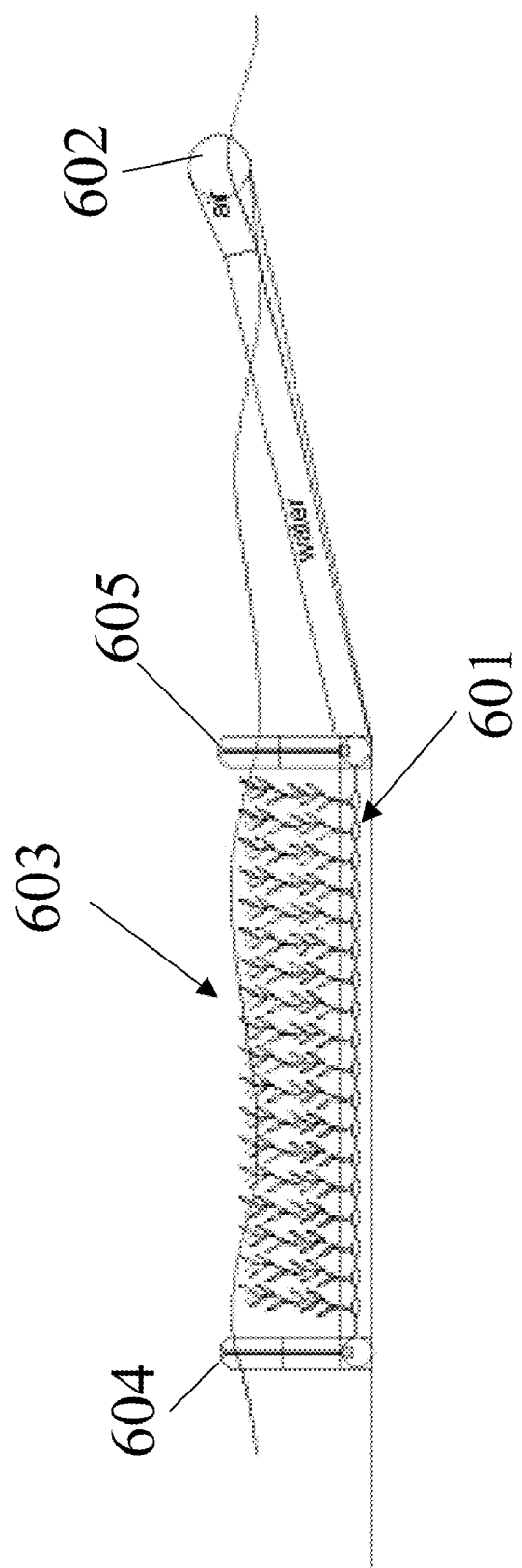
FIG. 7a illustrates a side view of the floatation collar.

The floatation collar 602 is a 2 m diameter nylon fabric tube inflated with air to 3 psi. It would float on the surface and be connected to the 20×20 m kelp frames by a branching set of 1 m diameter tubes filled with pressurized water as shown in FIG. 7a. The volume of air in the connecting tubes would be adjusted so that water line inside the tubes is roughly the same as outside.

Figure 7B:
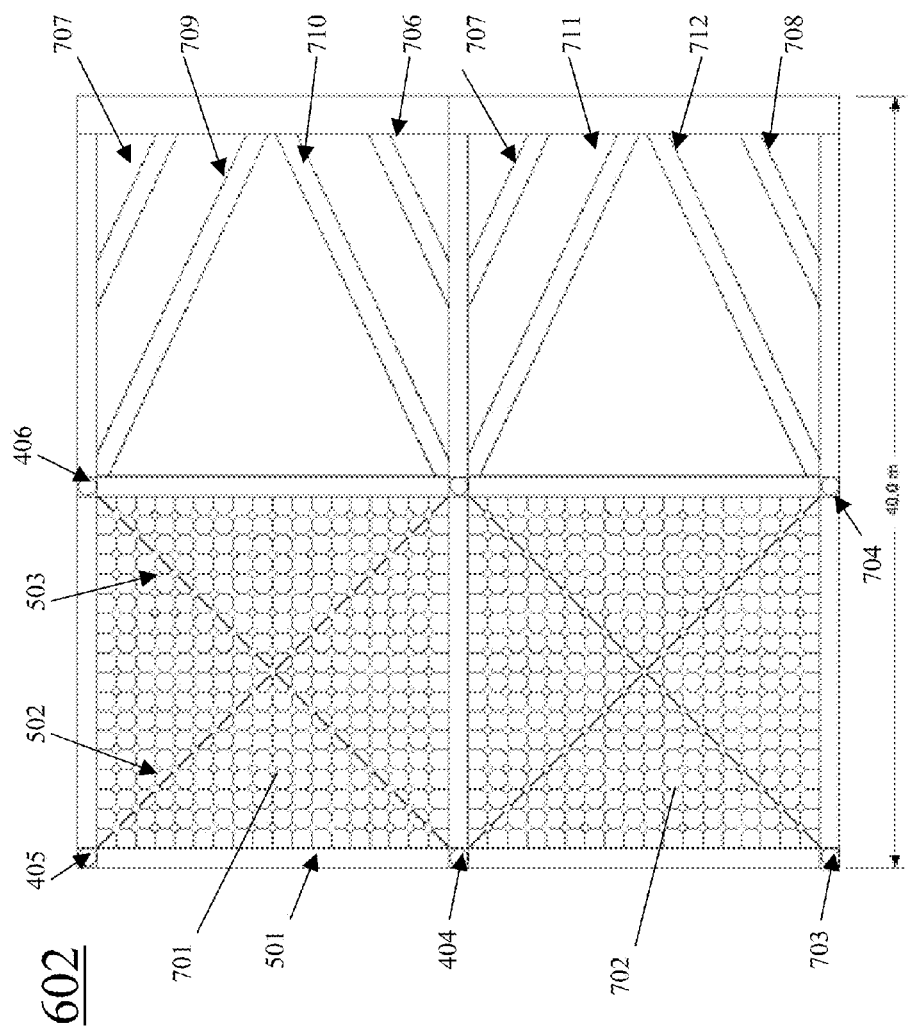
FIG. 7b illustrates a top view of the floatation collar.

The entire structure as shown in FIG. 7b would be partitioned into cells 701 and 702 to minimize the effect of a puncture in any of the pressurized tubes 501. Each cell 701 and 702 would require a sensor to measure the pressure in the cell, and a set of valves 404-406 and 703 and 704 connected to the network of pressurized air 705-708 and water hoses 709-712 to control air and water pressures and adjusts the buoyancy of the floatation buoys as the kelp crop matures. The size of the cells 701 and 702 and their number is to be determined as desired.

For free floating forms of algae, a simple water circulation system may be sufficient to harvest the algae. The free floating algae would be sucked into filters at the processing plants and waste water from processing the algae would be injected back into the lagoon near the periphery.

For types of algae that form dense floating mats, a fleet of harvesting barges would travel up and down the rows, scooping up the algae and squeezing out the water using rollers. These barges would be 18 m×18 m and equipped with bow and stern-sters as well as fore and aft-sters so that they can easily maneuver through the rows of floatation buoys. When full, each harvesting barge would deliver its cargo to the nearest available processing plant where it would be off-loaded. Since algae grow very fast, it may need to be harvested every day. This might take up to ten harvesting barges.

For kelp and other forms of seaweed that require mooring to the bottom, a 1 m×1 m square grid of cables would be suspended inside of the 20 m×20 m square frames. At each node of this 1 m grid, there is a holdfast for a single kelp plant. Thus, each frame can host up to 17×17=289 plants. In a 2 km square farm, there would be about 10,000 frames with at total of almost 3 million kelp plants.

As the kelp grows, it develops floatation bulbs that cause it to rise toward the surface and float in the sun. For a plant growing from a holdfast at 3 m depth, the buoyancy force of each kelp plant will be about 1.5 lb. Thus the holdfasts should weigh about 1.5 lb. each submerged, and the floatation buoys at each corner of the 20 m×20 m frame should have the capability to adjust buoyancy to keep the holdfast net at a desired depth as the buoyancy of the kelp plants changes. Buoyancy adjustments can be made by valves that add or release air from the buoys. A network of hoses inside the 1 m fabric tubes would supply pressurized water and air to needed to maintain the desired pressure in the structure and regulate buoyancy in the floatation buoys.

Occasionally, the biomass farm would be visited by a tanker that would off-load oil or ethanol via a hose. In exchange, the tanker could up-load fertilizer to holding tanks in the processing plants. Empty tankers need ballast water anyway, so delivery of liquid fertilizer would be free.

The structure shown in FIG. 1 covers 4 million square meters (roughly 1000 acres.) Assuming a production rate of 2,000 to 20,000 gal/acre/year, a farm this size could produce the equivalent of between 2 million and 20 million gallons of oil for biodiesel per year. This is equivalent to between 36,000 and 360,000 barrels of oil per year, or between 100 and 1000 barrels of oil per day. At $150 per barrel, this would return between $5.4 million and $54 million worth of product per year per farm. The current U.S. consumption of oil is about 20 million barrels per day. So it would take about 20,000 biofuel farms of this size to supply the entire U.S. need for oil, and about 80,000 farms this size to supply the entire world need for oil.

For most of the time, the kelp farm would drift with the current. However, power plants and propulsion units in bottom of the five processing plants (and perhaps sails on the roofs) would enable the farm to propel itself through the water. Differential-st in the five propulsion units would enable the farm to steer. This would give the farm the ability to navigate out of shipping lanes, stay clear of strong ocean currents, and avoid regions that are prone to hurricanes. Fortunately, the equatorial oceans are not often home to strong currents or hurricanes. An average speed of 1 knot is probably sufficient to stay clear of trouble. This would enable a kelp farm to navigate about 25 miles per day, or 8000 miles per year.

To avoid the occasional dangerous storm, the entire kelp farm could submerge to a depth such that storm energy would not damage the structure. This could be done by dumping air from the floatation collar and the floatation buoys so that the entire structure becomes negatively buoyant. Once it sinks to a safe depth, air would be pumped back into the floatation buoys to make the farm neutrally buoyant. Once the storm passes, more air would be pumped into the floatation buoys to bring the farm back to the surface.

Under this scenario, the farm would have to store sufficient compressed air to maintain negative buoyancy at a safe depth, and to return to the surface. Liquid $CO_2$ or some other gas that liquefies at room temperature and reasonable pressure may provide a solution to this problem. A snorkel might also be a solution for returning to the surface after the storm had passed.

Whenever the farm needs to sink below the surface, the fertilized water, free floating algae, and any fish in the lagoon would be lost, but kelp attached to holdfasts should survive.

It is anticipated that situations that require submerging the lagoon would be rare. Good weather predictions should be able to predict storms far enough in advance for the farm to avoid rough seas without interruption of normal operations. A good algorithm might be to cruise the southern half of the equatorial ocean during the northern hurricane season, and vice versa.

Further objectives and advantages of the invention will become apparent from a consideration of the drawings and ensuing description. Furthermore, other areas of art may benefit from this method and adjustments to the design are anticipated. Thus, the scope of the invention should be determined by the appended claims and their legal equivalents, rather than by the examples given.

We claim:

1. An apparatus for an open ocean floating algae farm consisting of:
   a ship having sides and a rear;
   an algae farm structured around said ship;
   said algae farm further comprised of:
      a plurality of transparent tubes creating a matrix of transparent tubes that circulates an algae broth of seawater saturated with $CO_2$, nutrients, and algae;
      a circulation path flows from the ship through the matrix of transparent tubes and back to the ship where the algae is filtered out to be processed, and nutrients and $CO_2$ are added to the seawater;
      the transparent tubes circulating the algae broth are supported by a matrix of one or more pressurized tubes filled with seawater; and
      the matrix of pressurized tubes is neutrally buoyant and is capable of being submerged just below an ocean surface.

2. The apparatus of claim 1 further comprising:
   a waterproof fabric base stretched over a top surface of the pressurized tubes;
      said water-proof fabric base supports the transparent tubes that circulate the algae broth, and also serves as a barrier to a vertical flow of seawater; and
   switchable flow check valves located in corner connectors are electronically switched open or closed to pump water upward for submerging, or downward for surfacing.

3. The apparatus of claim 1 wherein the internal pressure in the pressurized tubes would cause the matrix of pressurized tubes to be stiff in a horizontal plane, but flexible in a vertical dimension, with respect to an ocean surface, so as to conform to long ocean waves.

4. The apparatus of claim 1 wherein
   the ship has propulsion capabilities to allow the algae farm to navigate out of shipping lanes and away from hurricanes; and
   the pressurized support matrix of pressurized tubes would be attached to the ship's sides or rear and towing forces would be distributed throughout the matrix of pressurized tubes by a series of steel cables.

5. The apparatus of claim 1 wherein the algae farm is comprised of:
   a plurality of single cell elements; and
   the elements consist of pressurized fabric tubes that filled with seawater pressurized to about three psi.

6. The apparatus of claim 5 wherein the elements are twenty meters by twenty meters in size.

7. The apparatus of claim 5 wherein the elements consist of pressurized fabric tubes that are one meter in diameter.

8. The apparatus of claim 7 wherein a diameter ratio of an element size to the pressurized fabric tube is twenty to one.

9. The apparatus of claim 7, wherein the matrix of transparent tubes is further comprised of directional valves that pump water and algae through the transparent tubes.

10. The apparatus of claim 9 further comprising a fabric base attached to the transparent tubes that is penetrated in the corners by the directional valves.

11. The apparatus of claim 10 further comprising a robot moving through the transparent tubes and scrubbing them.

12. The apparatus of claim 10 further comprising a floatation collar around the matrix of pressurized tubes to prevent breaking waves from interacting with the transparent tubes.

* * * * *